(12) United States Patent
Thune

(10) Patent No.: US 6,350,454 B1
(45) Date of Patent: Feb. 26, 2002

(54) **ATTENUATED *PASTEURELLA PISCICIDA* VACCINE FOR FISH**

(75) Inventor: Ronald L. Thune, Baton Rouge, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 09/402,695

(22) PCT Filed: Apr. 9, 1998

(86) PCT No.: PCT/US98/07066

§ 371 Date: Oct. 8, 1999

§ 102(e) Date: Oct. 8, 1999

(87) PCT Pub. No.: WO98/46725

PCT Pub. Date: Oct. 22, 1998

Related U.S. Application Data

(60) Provisional application No. 60/043,768, filed on Apr. 11, 1997.

(51) Int. Cl.[7] .................. A61K 39/02; A61K 39/102; A61K 39/00; A61K 39/295; A01N 63/00
(52) U.S. Cl. .................. 424/200.1; 424/255.1; 424/93.4; 424/201.1; 424/203.4; 424/234.1; 424/184.1; 424/235.1; 424/827
(58) Field of Search .................. 424/255.1, 200.1, 424/9.2, 201.1, 203.1, 184.1, 234.1, 93.2, 93.4, 827, 235.1, 93.48

(56) References Cited

U.S. PATENT DOCUMENTS 5,747,309 A * 5/1998 Allan et al. .............. 435/172.3
5,780,448 A * 7/1998 Davis .......................... 514/44
6,010,705 A * 1/2000 Thune et al. ............. 424/234.1

FOREIGN PATENT DOCUMENTS

JP          5139994       * 1/1997

OTHER PUBLICATIONS

Curtin et al. FEMS Microbiol. Lett. 128: 75–80, 1995.*
Homchampa et al. Vet. Microbiol. 42: 35–44, 1994.*

* cited by examiner

*Primary Examiner*—S. Devi
(74) *Attorney, Agent, or Firm*—Bonnie J. Davis; John H. Runnels

(57) ABSTRACT

Live-attenuated vaccines against *Edwardsiella ictaluri* or against *Pasteurella piscicida* are disclosed. Both vaccines are incapable of reversion to virulence, because both are made by deletion mutations in the aroA gene, the purA gene, or both. These vaccines may be used not only to vaccinate fish against *Edwardsiella ictaluri* or *Pasteurela piscicida*, but also to serve as vectors to present antigens from other pathogens to the fish, thereby serving as vaccines against other pathogens as well, with no risk of infection by reversion to the virulent form of the pathogen in which the antigen occurs naturally.

15 Claims, No Drawings

ATTENUATED *PASTEURELLA PISCICIDA* VACCINE FOR FISH

The benefit of the Apr. 11, 1997 filing date of provisional application serial number 60/043,768 is claimed under 35 U.S.C. § 119(e) in the United States, and is claimed under applicable treaties and conventions outside the United States.

The development of this invention was partially funded by the United States Government under grant 93-34310-9057 and Hatch grant, both from the United States Department of Agriculture. The United States Government may have certain rights in this invention.

TECHNICAL FIELD

This invention pertains to fish vaccines, particularly to certain live-attenuated bacterial vaccines against fish pathogens.

BACKGROUND ART

Immune responses to live vaccines are generally of greater magnitude and of longer duration than those produced by killed or subunit vaccines. A single dose of a live-attenuated vaccine can provide better protection against later infection by the wild-type organism, because the attenuated organism persists and metabolizes within the host, and in some cases may replicate in the host for a time. See, e.g., M. Roberts et al., "Salmonella as Carriers of Heterologous Antigens," pp. 27–58 in O'Hagan (ed.), *Novel Delivery Systems for Oral Vaccines* (1994). Live vaccines better elicit cell-mediated immune responses, which can have a crucial role in controlling infections by intracellular pathogens. Injectable vaccines are impractical in most commercial fish culture due to extensive pond or cage production techniques, large numbers of individual animals, and low value per individual animal. Prior immersion or oral delivery of killed vaccines to fish has yielded inconsistent results. The invasion, persistence, and replication of live-attenuated vaccines has the potential to provide effective, inexpensive vaccines. R. Thune et al., "Studies on Vaccination of Channel Catfish, *Ictalurus punctatus*, against *Edwardsiella ictaluri*" pp. 11–23 in D. Tave et al. (ed.), *Recent Developments in Catfish Aquaculture* (1994).

An auxotrophic bacterium is a nutritional mutant requiring one or more growth factors to survive and replicate. Certain nutrients have limited availability in vertebrate tissues. A bacterium from an otherwise pathogenic species will be attenuated if it is made auxotrophic for such a limited nutrient. These auxotrophic mutants are potentially useful as live-attenuated vaccines.

Roberts et al. (1994) reviews the use of live-attenuated, transformed Salmonella as potential vectors for vaccinating humans and other mammals orally with heterologous antigens derived from other pathogens. Attenuated strains have been produced by a variety of routes, including strains with aroA or purA mutations. (The aroA gene encodes an enzyme needed in the biosynthesis of aromatic amino acids; and the purA gene encodes an enzyme needed in the biosynthesis of adenine.) See also C. Hornaeche, "Live Attenuated Salmonella Vaccines and Their Potential as Oral Combined Vaccines Carrying Heterologous Antigens," *J. Immunol. Meth.*, vol. 142, pp. 113–120 (1991); D. Sigwart et al., "Effect of a purA Mutation on a Efficacy of Salmonella Live-Vaccine Vectors," *Infection and Immunity*, vol. 57, pp. 1858–1861 (1989); and S. Hoiseth et al., "Aromatic-Dependent *Salmonella Typhimurium* are Non-Virulent and Effective as Live Vaccines," Nature, vol. 291, pp. 238–239 (1981). In mammalian hosts, however, adenine auxotrophic Salmonella purA mutants are less effective as vaccines than aroA mutants, possibly because purA mutants are overly attenuated due to the extremely low availability of adenine in mammalian tissues.

The channel catfish (*Ictalurus punctatus*) is the most important aquaculture species in the United States. R. Thune, "Bacterial Diseases of Catfish," Chapter 57 (pp. 511–520) in Stoskopf, M. K. (ed.), *Fish Medicine* (1993) reviews the major bacterial diseases encountered in commercial catfish aquaculture, the most serious of which is enteric septicemia of catfish (ESC). *Edwardsiella ictaluri*, the bacterium that causes ESC, was first described in 1979 after isolation from catfish farms in Georgia and Alabama. Since then it has been reported in every state that produces channel catfish commercially. *Edwardsiella ictaluri* was isolated from 46.2% of the channel catfish cases submitted to aquatic animal diagnostic laboratories in Alabama, Louisiana, and Mississippi during 1987–89.

The various *Edwardsiella ictaluri* strains that have been examined to date have been serologically and biochemically homogenous. As a result, killed bacterins have been evaluated as vaccines against ESC. A protective response has been inconsistent in field trials using killed preparations, and it has been suggested that prior, sub-clinical exposure of vaccinated fish to *E. ictaluri* during periods in which temperatures were not conducive to disease may have been an important factor in establishing this response; and that a similar response might not be seen in naive fish without a similar sub-clinical exposure. Thune et al. (1994). A variety of preparations were found to stimulate antibody production in these studies, but a positive antibody response did not always correlate to protective immunity unless very high titers of antibody were achieved. Protection of laboratory-reared *E. ictaluri*-free fish has not been demonstrated and no commercial vaccines for ESC are currently available.

A strong cell-mediated immune response could provide a more effective vaccination against ESC—both for the above reasons, and because *E. ictaluri* is a facultative intracellular pathogen.

Injection of a killed preparation with an adjuvant is one way to stimulate cell-mediated immunity (CMI), but because of the large numbers, small size, and low economic value of individual fish, this route of vaccination is not practical in commercial catfish production. Live-attenuated strains of pathogenic bacteria could potentially generate a strong CMI. In addition, attenuated strains of invasive pathogens may be delivered via oral and immersion routes, making their administration more economical. However, no previous vaccines have been reported to stimulate cell-mediated immunity against *E. ictaluri*.

Commercial farming of hybrid striped bass (*Morone saxatilis* x *Morone chrysops*) is a rapidly expanding aquaculture industry in the United States, the Mediterranean region, and southeast Asia, including Taiwan. In the United States, hybrid striped bass production increased from 3750 tons in 1994 to 7000 tons in 1996 (Hybrid Striped Bass Growers Association, personal communication). This fish is adapted for culture in both fresh and brackish water, resulting in the development of significant production of this hybrid species in coastal areas worldwide. In the United States, coastal hybrid striped bass farms are located in Louisiana, Texas, and Florida. In addition, United States producers ship millions of fry and fingerlings annually to marine and brackish water mariculture farms in Taiwan and in the Mediterranean region.

Along with the growth of this industry in coastal areas has come the emergence of the bacterial disease agent *Pasteurella piscicida*, which has seriously restricted the expansion of commercial aquaculture in warm water coastal areas. (*Pasteurella piscicida* has recently been renamed *Photobacterium damsela* subspecies piscicida. The historical nomenclature *Pasteurella piscicida* is used here.) Pasteurellosis was relatively unknown outside of Japan prior to 1990. In Japan pasteurellosis has caused losses in excess of $20 million annually in cultured yellowtail. The recent growth of coastal aquaculture in the United States and in the Mediterranean region has created ideal conditions for this highly pathogenic, halophilic organism. In Louisiana alone, 32 cases of heavy mortality in coastal hybrid striped bass farms have been reported in the last five years (Louisiana Aquatic Animal Diagnostic Lab case records), with two farms closing as a result of *P. piscicida* losses.

The gilthead seabream *Sparus aurata*, and seabass *Dicentrarchus labrax*, species that are farmed in Israel, Europe, and the Mediterranean, are also highly susceptible to *P. piscicida*. Production of hybrid striped bass, seabream, and seabass throughout the Mediterranean region is estimated to be tens of thousands of tons annually. *P. piscicida* has become a serious problem throughout the region.

Pasteurellosis is an acute, rapidly developing disease. Antibiotic treatments have often been impractical or ineffective. In addition, *P. piscicida* has quickly developed resistance to certain antibiotics. An effective vaccine would circumvent these problems. However, previous vaccinations of hybrid striped bass against *P. piscicida* using killed autogenous bacterins, Alpharma (Bellevue, Wash.) and AquaHealth (Ontario, Canada), delivered by immersion or injection, have not provided satisfactory results in the field (Dr. R. Ariav, personal communication).

Known host fishes of Pasteurellosis include the following: the temperate basses (Family Percichthyidae), including the white bass *Morone americanus*, the striped bass *Morone saxatilis*, and their hybrids; the sea basses (Family Serranidae), including the Japanese sea bass *Lateolabrax japonicus*, the Asian sea bass *Lates calcarifer*, and the European sea bass, *Dicentrarchus labrax*; the jacks (Family Carangidae), including yellowtail *Seriola quinqueradiata* and striped jack *Pseudocaranx dentex*; the filefishes (Family Balistidae), including the oval filefish *Navodan modestus*; and the seabream (Family Sparidae), including the black seabream *Acanthopagrus shlegeli*, the red sea bream *Pagrus major*, and the gilthead seabream *Sparus aurata*.

R. Kusuda et al., "The Efficacy of Attenuated Live Bacterin of *Pasteurella piscicida* against Pseudotuberculosis in Yellowtail," *Bull. Eur. Assoc. Fish Pathol.*, vol. 8, pp. 50–52 (1988) discloses that a degree of protective immunity was conferred by immersion vaccination of yellowtail with a *Pasteurella piscicida* strain that had been attenuated by serial passages on Brain Heart Infusion agar. These authors examined the response of yellowtail to formalin killed (FKB), heat killed (HKB), and the live-attenuated (ALB) bacterins, and found that the ALB reduced mortality to challenge from 81.3% in controls to 25.3% in vaccinated fish. The FKB and HKB reduced mortality to 57.3% and 78.7%, respectively. In addition, ALB increased phagocytic activity over controls from 4.0% to 19.0%, compared to 4.8% with HKB and 8.0% with FKB, while the increase in antibody level was similar for all three treatments. The authors stated that these results indicated that protection from *P. piscicida* infection may have been based on activation of phagocytes. The ALB vaccines of this study, however, were produced by serial passage on growth media, and are thus potentially susceptible to spontaneous reversion to virulence. The overall genetic change needed for reversion in such cases can be quite low—even a single point mutation may suffice.

U.S. Pat. No. 5,536,658 discloses a chondroitinase-attenuated Edwardsiella strain used as vaccine for catfish and other fish susceptible to Edwardsiella infection, administered by immersion, injection, or in feed.

U.S. Pat. No. 5,498,414 discloses attenuated *Aeromonas salmonicida* strains used as immersion vaccines for chinook salmon and rainbow trout. The attenuated strains were reported to lack a functional A-protein, a component of the cell membrane. The A-protein gene could be disrupted, for example, by insertion of a gene encoding an antigenic protein of another fish pathogen, thus potentially allowing the attenuated *Aeromonas salmonicida* to vaccinate fish against two pathogens.

E. Dunn et al., "Vaccines in Aquaculture: The Search for an Efficient Delivery System," *Aquacultural Engineering*, vol. 9, pp. 23–32 (1990) reviews various vaccine delivery methods for aquaculture.

P. Homchampa et al., "Construction and Vaccine Potential of an aroA mutant of *Pasteurella haemolytica*," *Veterinary Microbiology*, vol. 42, pp. 35–44 (1994) discloses the use of an attenuated *Pasteurella haemolytica* mutant with an aroA mutation to immunize mice, as a model for a cattle vaccine against bovine pneumonic pasteurellosis.

L. Vaughan, "An Aromatic-Dependent Mutant of the Fish Pathogen *Aeromonas salmonicida* Is Attenuated in Fish and Is Effective as a Live Vaccine against the Salmonid Disease Furunculosis," *Infection and Immunity*, vol. 61, pp. 2172–2181 (1993) discloses that an attenuated *Aeromonas salmonicida* with an aroA mutation was not virulent when injected intramuscularly into Atlantic salmon; and that intraperitoneal vaccination with the attenuated strain conferred protective immunity to brown trout against infection by a virulent A. salmonicida strain. See also L. Vaughan et al., "Field Testing of a Novel Live-Attenuated Furunculosis Vaccine in Atlantic Salmon (*Salmo salar*), in Book of Abstracts, *Biotechnological Approaches to the Culture and the Diseases of Fish and Shellfish* (Cork, a Ireland, 14–17 September 1992).

C. Lobb, "Secretory Immunity Induced in Catfish, *Ictalurus punctatus*, Following Bath Immunization," *Developmental and Comparative Immunology*, vol. 11, pp. 727–738 (1987) discloses that catfish developed a mucosal immune response when immersed in an antigen bath containing dinitrophenylated-horse serum albumin, but that few of the catfish developed a humoral response.

J. Plumb et al., "Vaccination of Channel Catfish, *Ictalurus punctatus* (Rafinesque), by Immersion and Oral Booster against *Edwardsiella ictaluri*," *J. Fish Diseases*, vol. 16, pp. 65–71 (1993) discloses a formalin-killed *Edwardsiella ictaluri* immersion vaccine that produced humoral immunity in *Ictalurus punctatus*, with or without a subsequent oral booster.

R. Thune et al., "Studies on Vaccination of Channel Catfish, *Ictalurus punctatus*, against *Edwardsiella ictaluri*" pp. 11–23 in D. Tave et al. (ed.), Recent Developments in *Catfish Aquaculture* (1994) discloses a formalin-killed *Edwardsiella ictaluri* immersion vaccine for the catfish *Ictalurus punctatus*, with or without a subsequent oral booster.

DISCLOSURE OF INVENTION

We have discovered effective live-attenuated vaccines against *Edwardsiella ictaluri*. We have also discovered effective live-attenuated vaccines against *Pasteurella piscicida*. Both vaccines are incapable of reversion to virulence. Both were made by large deletion mutations either in the aroA gene or in the purA gene.

We have also discovered that these vaccines may be used not only to vaccinate fish against *Edwardsiella ictaluri* or *Pasteurella piscicida*, but also to serve as vectors to present antigens from other pathogens to the fish immune system, thereby serving as vaccines against other pathogens as well, with no risk of infection by reversion to the virulent form of the pathogen in which the antigen occurs naturally.

MODES FOR CARRYING OUT THE INVENTION

Production of Live-attenuated *Edwardsiella ictaluri*

A. Bacterial Strains and Plasmids Used

Bacterial strains and plasmids used in these experiments are listed with their sources in Table 1.

TABLE 1

Bacterial Strains and Vectors

*Escherichia coli*

1. CC118 λpir; Δ(ara-leu) araD ΔlacX74 galE galK phoA20 thi-1 rpsE rpoB argE (Am) recA λpir phage lysogen; from Herrero et al., "Transposon Vectors Containing Non-Antibiotic Resistance Selection Markers for Cloning and Stable Chromosomol Insertion of Foreign Genes in Gram-negative Bacteria," Journal of Bacteriology, vol. 172, pp. 6557–6567 (1990).
2. SM10 λpir; Km thi-1 thr leu tonA lacY supE recA::RP4-2-Tc::Mu λpir phage lysogen; from Herrero et at., (1990).

*Edwardsiella ictaluri*

1. 93-146; wild-type *E. ictaluri* isolated in 1993 from moribund channel catfish in a natural outbreak of ESC on a commercial farm; from LSU Aquatic Animal Diagnostic Laboratory.
2. LSU-E1 (ATCC No. 55947); derived from 93–146, except ΔaroA::Tn903 ($Km^r$) as described below.
3. LSU-E2 (ATCC No. 55948); derived from 93–146, except ΔpurA::Tn903 ($Km^r$) as described below.

Plasmids 1. pEI11; Ap, pBluescript derivative with 1104 base pair *E. ictaluri* purA PCR product inserted in EcoR V site; present work.
2. pEI14; Km, pBK-CMV derivative with 5.6 kilobase segment of the *E. ictaluri* chromosome inserted into a BamH I site, the 5.6 kb segment containing the purA gene; present work.
3. pEI15; Ap, pBluescript derivative with 3.5 kilobase Not I fragment containing the purA gene inserted in Not I site; present work.
4. pNK2859; Ap Km, derivative of pBR322 with mini-Tn10Km (TN903 Km), $Ptac^P$; from Kleckner et al., "Uses of Transposons with Emphasis on Tn10," Methods in Enzymology, vol. 204, pp. 139–180 (1991).
5. pEI16; Ap Km, pEI15 derivative with 598 base pair Nar I deletion in the purA gene and 1.7 kilobase BamH I segment of Tn903 inserted in NarI deletion site; present work.
6. pGP704; Ap, pBR322 derivative with R6K ori, mob RP4, polylinker from M13 tg131; from Miller et al., "A Novel Suicide Vector and its Use in Construction of Insertion Mutants: Osmoregulation of Outer Membrane Proteins and Virulence Determinants in *Vibrio cholerae* requires toxR," Journal of Bacteriology, vol. 170, pp. 2575–2583 (1988).
7. pEI17; Ap Km, pGP704 derivative with 4.6 kilobase Not I fragment containing modified *E. ictaluri* purA gene inserted in EcoR V site; present work.
8. pEI21a; Km, pBK-CMV derivative with a 2789 base pair segment of the *E. ictaluri* chromosome inserted in the BamH I site and containing the aroA gene; present work.
9. pEI22; Ap, pBluescript derivative with 2789 base pair segment of the *E. ictaluri* chromosome inserted in the Not I site and containing the aroA gene; present work.
10. pEI23; Ap Km, pEI22 derivative with a 259 base pair Nar I fragment deleted from the aroA gene and a 1.7 KB BamH I $Km^r$ fragment of Tn903 inserted in the Nar I deletion site; present work.
11. pEI24; Km, pGP704 derivative carrying ΔaroA::Tn903 ($Km^r$) as in pEI23; present work.

B. Isolation of Wild Type

The parental organism for the two live-attenuated vaccines is *Edwardsiella ictaluri* strain 93–146, which was isolated from catfish undergoing an ESC epizootic in north Louisiana in May 1993. *Edwardsiella ictaluri* strain 93–146 was confirmed using standard microbiological methods and API 20e test strips, generating a code of 4004000. The strain was sensitive to oxytetracycline, Romet, erythromycin, nitrofurantoin, and kanamycin. No genetic modifications were made in *E. ictaluri* strain 93–146 prior to construction of the two attenuated mutants described below.

C. Production of the aroA Mutant

This mutant strain, LSU-E1 (ATCC No. 55947), had a 259 bp deletion within the 1284 base pair aroA gene. Base pairs 541–801 of the aroA gene were deleted. The mutant required supplementation with aromatic metabolites, namely para-aminobenzoic acid, di-hydroxybenzoic acid, and hydroxybenzoic acid, in *E. ictaluri* minimal media (EI-MM), as otherwise described in L. Collins et al., "Development of a Defined Minimal Medium for the Growth of *Edwardsiella ictaluri*," Applied and Environmental Microbiology, vol. 62, pp. 848–852 (1996). An inserted marker gene for this mutant was a 1697 bp BarnH1 kanamycin resistance fragment from Tn903.

The deletion mutant was constructed using the following technique. An *E. ictaluri* genomic library was initially created in an intermediate cloning vector, the phagemid λZAP® (Stratagene Inc., La Jolla, Calif.), carrying plasmid pBKCMV. Plasmid pEI21a, containing a 2.8 kb insert, was selected from the genomic library by complementation in an aroA mutant of *E. coli*. The entire insert was sequenced, and was determined to be 2789 bp long. The complete *E. ictaluri* aroA gene was determined to occur at base pairs 1238 to 2524 of the insert; the gene was 1287 nucleotides long, with 68% identity to the *E. coli* aroA gene. The fragment was sub-cloned in pBluescript (Stratagene, Inc., La Jolla, Calif.) to facilitate subsequent manipulations, and the resulting plasmid was named pEI22. Sequence analysis indicated that the restriction endonuclease Nar I cut pEI22 at base pairs 1780 and 2038 of the insert in pEI22, but would not cut the pBluescript vector. Consequently, pEI22 was digested with the endonuclease Nar I to create a 259 bp deletion in the aroA gene, and also to linearize pEI22. The Nar I overhangs of the linearized plasmid were filled in using Klenow fragment, and the kanamycin marker gene was inserted by blunt end ligation, creating pEI23.

The 2364 bp fragment containing the mutated gene was ligated into the π-protein based suicide vector pGP704 for transfer to wild-type *E. ictaluri* by RP4-mediated conjugation and homologous recombination, creating pEI24. Transconjugates were selected on media containing kanamycin, with colistin added to counter-select against the *E. coli* donor. Because the suicide vector contained an ampicillin resistance marker, $kan^r$ transconjugates were replica-plated to media containing ampicillin to establish ampicillin sensitivity, to verify that the vector had not been maintained.

After isolation of $Kan^r/amp^s$ colonies, the strain *E. ictaluri* LSU-E1 (ATCC No. 55947) was confirmed to require supplementation with aromatic metabolites in EI-MM. The construct was tentatively confirmed using primers from flanking sequences and from the kanamycin marker gene to amplify specific gene fragments using the polymerase chain reaction (PCR). Final confirmation of the construct was obtained by sequencing the PCR products and demonstrating alignment to the aroA:kan sequence. Specifically, PCR using primer aro-5, designed to anneal to base pairs 1507–1524 of the negative strand of the aroA gene, and primer kan+, designed to anneal to base pairs 1399–1417 of the positive strand of the kan marker sequence, resulted in the amplification of a 1279 bp fragment consisting of 1003 bp of the kan marker and 276 bp of the amino terminus of the aroA gene. Reactions using primer aro+3, designed to anneal to base pairs 2052–2069 of the positive strand of the aroA gene, and primer kan-, designed to anneal to 2007–2024 of the negative strand of the kan marker gene, resulted in amplification of a 1564 bp fragment consisting of 231 bp of the carboxyl terminus of the aroA gene and 1333 bp of the kan marker gene.

Stability of the LSU-E1 construct was demonstrated by growing it in 30 successive passages in culture tubes containing 5 mL Brain Heart Infusion Broth (BHI) without kanamycin. A 100 µL aliquot from overnight cultures was used to inoculate each subsequent tube. At pass 30, two 5 mL cultures were pelleted in a centrifuge, suspended in 100 mL saline, and spread on EI-MM to detect revertants to the wild-type phenotype, i.e., the ability to grow on EI-MM without aromatic metabolite supplementation. Prior to spreading on EI-MM, an aliquot was removed and serially diluted to determine colony forming units (cfu)/mL in the concentrated suspensions. A total of $5.67 \times 10^{10}$ cfu's plated on minimal media after 30 passes in BHI yielded no revertant colonies.

A sample of the bacterium LSU-E1 was deposited with the American Type Culture Collection (ATCC), 10801 University Boulevard, Manassa, Va. 20110-2209 on Apr. 9, 1997, and was assigned ATCC Accession No. 55947. This deposit was made pursuant to a contract between ATCC and the assignee of this patent application, Board of Supervisors of Louisiana State University and Agricultural and Mechanical College. The contract with ATCC provides for permanent and unrestricted availability of the bacterium to the public on the issuance of the U.S. patent describing and identifying the deposit or the publication or the laying open to the public of any U.S. or foreign patent application, whichever comes first, and for availability of the progeny of the bacterium to one determined by the U.S. Commissioner of Patents and Trademarks to be entitled thereto under pertinent statutes and regulations. The assignee of the present application has agreed that if the bacterium on deposit should die or be lost or destroyed when cultivated under suitable conditions, it will be promptly replaced on notification with a viable culture of the same bacterium.

D. Production of the purA Mutant

*Escherichia coli* was grown at 37° C. with Luria-Bertani (LB) broth and agar plates following the method of Sambrook et al., *Molecular Cloning: a Laboratory Manual*, Cold Spring Harbor Laboratory Press, Cold Spring Harbor, N.Y. (1989). *Edwardsiella ictaluri* was grown at 28° C. with BHI and agar plates, or with trypticase soy agar (TSA) II plates with 5% sheep blood. LAMBDAZAP® Express bacteriophage (Stratagene, La Jolla, Calif.) were grown in *E. coli* XL1-Blue MRF' (Stratagene) with NZYM® agar plates and NZYM® top agarose. EI-MM broth and agar plates with and without supplemented adenine (25 µg/ml) were used for nutritional characterization of *E. ictaluri* strains. The API 20E system (bioMerieux Vitek, Hazelwood, Mo.) was used for species identification and biochemical characterization of *E. ictaluri* strains. Conjugations between *E. ictaluri* and *E. coli* were grown at 28° C. on LB plates.

The F' episome was maintained in *E. coli* XL1-Blue MRF' with tetracycline selection at 12.5 µg/ml. Ampicillin at 200 µg/mL was used to maintain pBluescript (Stratagene), pGP704, and their derivatives. Kanamycin at 50 µg/mL was used to maintain plasmids derived from the pBK-CMV phagemid and plasmids carrying Tn903. Colistin at 10 µg/mL was used for counterselection against *E. coli* SM10 λpir following conjugations. For blue-white screening of DNA cloned into pBluescript, *E. coli* XL1-Blue MRF' was spread on LB plates with 100 µL of 100 mM IPTG and 40 µL of 2% X-gal.

*Edwardsiella ictaluri* genomic DNA was prepared from overnight 100 mL cultures using a modification of the protocol by Ausubel et al. (eds.), *Current Protocols in Molecular Biology*, John Wiley & Sons, New York (1994). Bacteria were pelleted by centrifugation at 5000×g for 10 minutes and resuspended in 9.5 mL TE (10 mM Tris and 1 mM EDTA, pH 8.0). Cells were lysed in 0.5% SDS and 100 µg/mL of proteinase K at 50° C. for 2 hours. Following the addition of 1.8 mL of 5 M NaCl and 1.5 mL of 0.7 M NaCl/10% CTAB (hexadecyltrimethyl ammonium bromide), the lysate was incubated for 20 minutes at 65° C. An equal volume of 25:24:1 phenol/chloroform/isoamyl alcohol was added, and the aqueous phase was separated by centrifugation at 4000×g for 20 minutes in a swinging bucket rotor. The aqueous layer containing genomic DNA was transferred to a fresh tube, and an equal volume of 24:1 chloroform/isoamyl alcohol was added. The aqueous phase was separated again by centrifugation and transferred to a fresh tube. DNA was precipitated by addition of sodium acetate (pH 5.5) to 0.3 M followed by addition of an equal volume of isopropanol. The precipitated DNA was spooled from the aqueous-isopropanol interface using a sterile glass rod, washed in 70% ethanol, and resuspended in 3 mL of TE buffer.

Small and large scale preparations of plasmids were conducted using alkaline lysis as described in Sambrook et al. (1989), and large scale plasmid preparations were purified using QIAGEN-tip 100 columns (Qiagen, Chatsworth, Calif.). Restriction endonucleases, DNA polymerase I Klenow fragment, calf intestinal alkaline phosphatase (CIP), and T4 DNA ligase were obtained from New England Biolabs (Beverly, Mass.) and were used according to the manufacturer's protocols. DNA fragments were eluted from agarose gels using the ELU-QUICK® DNA Purification Kit (Schleicher & Schuell, Keene, N.H.).

Both *E. coli* and *E. ictaluri* were prepared for electroporation using the protocol of Ausubel et al. (1994). Washed *E. coli* were transfected by electroporation in 0.2 cm cuvettes at 2.5 kV and 25 µF, with the pulse controller set at 200 ohms. Washed *E. ictaluri* were electroporated using the same protocol at 1.75 kV. Bacteria were recovered for 1 hour in BHI broth at 37° C. (*E. coli*) or 28° C. (*E. ictaluri*) before being spread on selective media.

An 1104 base pair fragment of the *E. ictaluri* purA gene was amplified from genomic *E. ictaluri* DNA using PCR primers derived from conserved regions of the *E. coli* purA gene, as determined by alignments ofpublishedpurA gene sequences. See Wolfe et aL, "Nucleotide Sequence and Analysis of the purA Gene Encoding Adenylosuccinate Synthetase of *Escherichia coli* K12, " *J. Biol. Chem.*, vol. 263, pp. 19147–19153 (1988); see also Mantsala et al., "Cloning and Sequence of *Bacillus subtilis* purA and guaA, Involved in the Conversion of IMP to AMP and GMP," *J. Bacteriology*, vol. 174, pp. 1883–1890 (1992); and Kusano et al., "Identification of the purA Gene Encoding Adenylosuccinate Synthetase in *Thiobacillus ferrooxidans*," *Current Microbiology*, vol. 26, pp. 197–204 (1993). All PCR reactions were conducted on a Perkin Elmer DNA Thermal Cycler 480 using AMPLITAQ® DNA Polymerase at pH 8.5, with a magnesium concentration of 1.5 mM, 125 ng of template DNA per reaction, a 0.25 µM concentration of each primer, and a 30 µM concentration of each dNTP. Cycle conditions were 95° C. for 30 seconds, 53° C. for 45 seconds, and 72 ° C. for 45 seconds for 35 cycles; with an initial denaturation step at 95° C. for 2 minutes, and a final extension step at 72° C. for 10 minutes. To increase total PCR product yield, a second PCR was carried out using the product from the first PCR as the template (0.5 µL of a ¹⁄₁₀ dilution) under the same conditions. Prior to ligation into pBluescript, the purA PCR product was purified using the ELU-QUICK® DNA Purification Kit to remove excess primers and dNTPs. Primers for both PCR and sequencing were synthesized using solid-phase cyanoethyl phosphoramidate chemistry on a Perkin Elmer/Applied Biosystems DNA Synthesizer Model 394.

Agarose gels were prepared for Southern hybridization using the protocol of Ausubel et al. (1994), and DNA was transferred to NYTRAN® Plus 0.45 µm nylon membranes using a POSIBLOT® 30—30 pressure blotter and pressure control station (Stratagene). The 1104 base pair *E. ictaluri* purA PCR fragment was denatured by boiling, and was labeled directly with horseradish peroxidase using the ECL™ direct nucleic acid labeling and detection system (Amersham Life Science, Arlington Heights, Ill.). Labeled PCR fragments were used as a probe for plaque hybridization and Southern hybridization. Prehybridization, hybridization, and stringency washes were all performed in tubes at 41° C. according to the ECL™ protocol using a hybridization oven with an integral rotisserie device, followed by chemiluminescent detection.

The *E. icraluri* genomic library was constructed by cloning *E. ictaluri* genomic DNA after partial digestion with Sau3A I into the BamH I site of λZap™ Express. *E. coli* XL1-Blue MRF was transfected with the library according to the λZap™ Express protocol, and was spread on three plates containing approximately 11,000 plaque forming units (pfu) per plate. Plaques were transferred to Nytran Plus™ 0.45 Am nylon membranes (Schleicher & Schuell), and phage DNA was released, denatured, and fixed to the membranes according to the manufacturer's protocol. The library was screened by DNA hybridization using the labeled 1104 base pair *E. ictaluri* purA PCR fragment as a probe One positive plaque was purified by screening three additional times. The purified clone was excised as a phagemid in *E. coli* XLOLR according to the Stratagene protocol and named pEI14. Southern hybridization was used to confirm that the phagemid contained the purA gene.

The complete sequences of the purA gene and of the flanking chromosomal sequence (carried on plasmid pEI14) were determined using the ABI PRISM® Dye Terminator Cycle Sequencing Ready Reaction Kit (Perkin Elmer, Foster City, Calif.). Extension products were purified using Centri-Sep™ spin columns (Princeton Separations, Adelphia, N.J.), and were then dried in a vacuum centrifuge and stored at –20° C. Sequencing reactions were resolved using the ABI PRISM™ 310 Genetic Analyzer. Initial sequence reactions used primers based on the known sequence of the *E. ictaluri* purA PCR fragment, and subsequent sequence reactions used primers that were produced from the generated sequence. Reaction products were purified using CENTRICON® 100 concentrators (Amicon, Beverly, Mass.) prior to sequencing. Each reaction was diluted in 2 mL of sterile distilled water and concentrated according to the manufacturer's protocol.

A portion of the pEI14 insert was subcloned into pBluescript to facilitate mutagenesis of the *E. ictaluri* purA gene. Plasmid pEI14 DNA was digested with Not I, and the resulting 3.5 kb fragment was ligated into Not I-digested CIP-treated pBluescript. *E. coli* XL1-Blue MRF was transfected with the ligation mix by electroporation, and was spread on LB/Amp/Tet plates with IPTG and X-gal for blue-white screening. The resulting 6.5 kb plasmid was designated pEI15.

Plasmid pNK2859 DNA was digested with BamH I to isolate a 1.7 kilobase fragment containing the Tn903 kanamycin resistance gene, and pEI15 DNA was digested with Nar I to remove a 598 base pair fragment from the purA gene sequence. Both digests were treated with Klenow fragment in the presence of dNTPs to fill in the sticky ends. The 5.9 kilobase band from pEI15 was blunt end-ligated to the 1.7 kilobase band from pNK2859, and *E. coli* XL1-Blue MRF was transfected with the ligation mix by electroporation and spread on LB/Amp/Kan plates. This 7.6 kilobase plasmid was designated pEI16.

Finally, the pEI16 insert was subcloned into the suicide plasmid pGP704. Plasmid pEI16 DNA was digested with Not I to remove the 4.6 kilobase insert, and the Not I sites were filled in using Klenow fragment. This fragment was blunt end-ligated into the EcoR V site of pGP704, and *E. coli* CC118 λpir was transfected with the ligation mix by electroporation and spread on LB/Amp/Kan plates. The resulting 8.5 kilobase plasmid carrying the ΔpurA::Km$^r$ construct and over 2200 bp of flanking *E. ictaluri* chromosomal sequence was designated pEI17. Plasmid pEI17 was subsequently transferred to *E. coli* SM10 λpir by electroporation.

Conjugation was conducted between *E. coli* strain SM10 λpir and *E. ictaluri* 93–146 using a modification of the protocol of Herrero et al., "Transposon Vectors Containing Non-Antibiotic Resistance Selection Markers for Cloning and Stable Chromosomol Insertion of Foreign Genes in Gram-negative Bacteria," *Journal of bacteriology*, vol. 172, pp. 6557–6567 (1990). The cell densities of an *E. ictaluri* culture grown to mid-log phase, and of an overnight SM10 λpir culture were estimated by measuring absorbance at 600 nm, and the two cultures were mixed in 5 mL of 10 mM $MgSO_4$ in a 2:1 ratio (approximately $1.3 \times 10^8$ *E. ictaluri* and $6.5 \times 10^7$ *E. coli*). Bacteria were collected on a GELMAN® 0.45 µM Metricel filter, transferred to the surface of an LB plate, incubated overnight at 28° C., and resuspended in 5 mL of 10 mM $MgSO_4$. The total number of *E. ictaluri* in this suspension was determined by dropping 20 µL samples from serial dilutions on LB/Col plates and counting after 2 days. Mutant *E. ictaluri* colonies were selected by spreading 100 µL aliquots of the suspension on LB/Kan/Col plates. Two hundred fifty kanamycin resistant colonies were screened for ampicillin sensitivity by transferring colonies to LB/Amp/Kan plates.

Plasmid pEI17 was transferred into *E. ictaluri* using the RP4 origin of transfer by conjugation with *E. coli* SM10 λpir as the donor strain. The plasmid pEI17 did not persist in *E. ictaluri*, as judged by sensitivity to ampicillin, plasmid preparations, and negative PCR results using internal pGP704 primers from the ampicillin resistance gene. In one conjugation, 1865 kanamycin-resistant *E. ictaluri* colonies were isolated from approximately $9.8 \times 10^6$ *E. ictaluri* cfu spread on selective media. Of 250 kanamycin-resistant colonies screened, four colonies were identified that were also ampicillin sensitive, indicating a double crossover recombination event and incorporation of the deletion/insertion mutation into the chromosome with concurrent loss of the suicide plasmid. All four mutants failed to grow in minimal medium, but each of the four grew in minimal medium supplemented with 25 µg/mL adenine. Otherwise, the mutants maintained the wild-type phenotype, as determined using API 20E strips. They also maintained the same plasmid profile as wild type *E. ictaluri*, with no evidence of any persistence of the suicide plasmid.

Stability of the adenine auxotrophic phenotype in *E. ictaluri* LSU-E2 (ATCC No. 55948) was demonstrated by growing it in 30 successive passages in culture tubes containing 5 mL BHI without kanamycin. The final two 5 mL cultures were pelleted by centrifugation in a swinging bucket rotor at 4750×g for 10 minutes. The pellets were resuspended in 0.9 mL of sterile 0.9% saline, and nine 100 µL aliquots from each were spread on *E. ictaluri* minimal media plates, and were checked for growth 4 days later. Serial dilutions of the suspension were dropped in 20 µL aliquots on BHI plates, and were counted 2 days later.

*Edwardsiella ictaluri* 93–146 genomic DNA, and genomic DNA from LSU-E2 were used as templates for a series of PCR amplifications to confirm the genotype of LSU-E2. Plasmid pEI17 DNA was used as a positive control for the reactions. Primer concentrations of 0.5 µM, dNTP concentrations of 100 µM, and 100 ng of template DNA were used for each reaction. Cycle conditions were 95° C. for 30 seconds, 59° C. for 1 minute, and 72° C. for 3 minutes for 35 cycles; with an initial denaturation step at 95° C. for 2 minutes, and a final extension step at 72° C. for 10 minutes.

Amplification of a portion of the Tn903 kanamycin resistance gene using primers 903Kan+ and 903Kan− yielded the predicted 624 base pair band from mutant chromosomal DNA, indicating that the Tn903 gene had been successfully incorporated into the LSU-E2 chromosome. Only nonspecific bands were obtained from control, wild-type *E. ictaluri*. Amplification using primers pBRAmp+ and pBRAmp− yielded only non-specific bands from both LSU-E2 and wild-type *E. ictaluri*, indicating the ampicillin resistance gene from pEI17 had not been incorporated into the chromosome. Plasmid pEI17 DNA, which was used as a positive control for this reaction, yielded the predicted 709 base pair band for the ampicillin resistance gene. Primers PurAU1 and 903Kan+ amplified the 3' end of the Tn903 insert and flanking purA gene sequence, resulting in a 1191 base pair fragment from LSU-E2 DNA and no amplification for wild-type DNA. Primers PurAM11 and Tn903M2 yielded a 587 base pair fragment from LSU-E2 DNA containing the 5' end of the Tn903 insert and flanking purA gene sequence; comparable results were again negative for wild-type DNA. Sequencing of the 1191 base pair PurAU1/903Kan+ fragment and the 587 base pair PurAM11/Tn903M2 fragment demonstrated the purA gene sequence up to the Tn903 ligation site, at which point the Tn903 gene sequence began for both fragments.

A sample of the bacterium LSU-E2 was deposited with the American Type Culture Collection (ATCC), 1801 University Boulevard Mansas, Va. 20110-2209 on Apr. 9, 1997, and was assigned ATCC Accession No. 55948. This deposit was made pursuant to a contract between ATCC and the assignee of this patent application, Board of Supervisors of Louisiana State University and Agricultural and Mechanical College. The contract with ATCC provides for permanent and unrestricted availability of the bacterium to the public on the issuance of the U.S. patent describing and identifying the deposit or the publication or the laying open to the public of any U.S. or foreign patent application, whichever comes first, and for availability of the progeny of the bacterium to one determined by the U.S. Commissioner of Patents and Trademarks to be entitled thereto under pertinent statutes and regulations. The assignee of the present application has agreed that if the bacterium on deposit should die or be lost or destroyed when cultivated under suitable conditions, it will be promptly replaced on notification with a viable culture of the same bacterium.

E. Virulence in Specific Pathogen Free Channel Catfish

Egg masses were obtained from commercial channel catfish producers with no history of ESC outbreaks. The eggs were disinfected with 100 ppm free iodine, and were hatched in closed recirculating systems in a specific pathogen free (SPF) laboratory. Fish were maintained in the SPF laboratory through either the fingerling or juvenile stage. Prior to experimental infection, SPF fish were restocked into 20 liter flow-through tanks in separate challenge laboratories, and were acclimated for 2 to 4 weeks. Flow rates in the challenge tanks were maintained at approximately 300–400 mL per minute using dechlorinated municipal water, with temperatures maintained at 24–26° C.

In two separate experiments, SPF channel catfish fingerlings (approximately 5 grams per fish) were stocked at a rate of ten per tank and randomly assigned to treatment groups, with three tanks per treatment. In Experiment 1, treatment groups were experimentally infected with a specified dose of wild-type E. ictaluri or LSU-E2 by one of three routes: immersion, injection, or oral. In Experiment 2, treatment groups were experimentally infected with a specified dose of wild-type E. ictaluri or LSU-E1 by one of three routes: immersion, injection, or oral.

Both mutants were avirulent when administered by injection at a dose of $10^6$ colony forming units (cfu) per fish. By comparison, the wild-type E. ictaluri strain caused 96.7–100% mortality at intraperitoneal injection doses of $10^5$ cfu and $10^6$ cfu, 72.4–100% at $10^4$ cfu, 56.6–73.3% at $10^3$ cfu, and 43.3–56.6% at $10^2$ cfu. Mortality with the mutant strains could only be demonstrated when ~$10^7$ bacteria were injected per fish, a dose that, with minimal replication in the host, approximated total bacterial load in fish that die from a wild-type infection.

Both mutants were avirulent when administered by immersion at a dose of $10^7$ cfu/ml, while immersion in $10^7$ cfu/mL of the wild type caused 63.3–100% mortality. Both mutants were avirulent at oral doses of $10^8$ cfu per fish, while wild-type bacteria caused 20.7.–26.7% mortality at the same dose.

Results of the challenge experiments are summarized in Table 2. Mortality in all unchallenged negative controls was 0.0% (control data therefore not listed in table).

F. Tissue Distribution and Persistence

SPF channel catfish fingerlings were stocked at a rate of ten per tank, and were randomly divided into three treatment groups with three tanks per treatment. One of the treatment groups was experimentally infected by immersion with wild-type E. ictaluri, one was experimentally infected with LSU-E2 E. ictaluri, and the third was experimentally infected with LSU-E1 E. ictaluri. Wild-type, LSU-E2, or LSU-E1 E. ictaluri bacterial culture was added directly to the flow-through tanks at doses corresponding to approximately $3.5\times10^7$ cfu/mL for wild-type, $6.7\times10^6$ cfu/mL for LSU-E2, and $2.1\times10^7$ cfu/mL for LSU-E1. Water flow was stopped for 15 minutes following initial exposure, and was then resumed.

At 2 hours, 6 hours, 12 hours, 24 hours, 2 days, and 3 days post-exposure, one fish was removed from each tank and was euthanized by transfer to water containing 1 g/L MS-222. In the wild-type treatment the study was extended and fish were also collected on days 4 and 5 (only two fish were sampled on day 5). One fish was collected from each tank prior to experimental infections for a zero hour sample. Using aseptic techniques, samples were taken of liver, spleen, head kidney, and trunk kidney from each fish. The samples were suspended in 0.5 mL sterile 0.9% saline solution, weighed, and pulverized. The resulting suspension was serially diluted in 0.9% saline solution in triplicate using 96-well plates, and 20 $\mu$L aliquots were dropped on BHI plates for quantification. Colonies were counted after incubation for 48 hours. Edwardsiella ictaluri and other bacterial species were identified using the API 20E system.

Adenine auxotrophic E. ictaluri strain LSU-E2, or aromatic auxotrophic E. ictaluri strain LSU-E1, as appropriate, was isolated from the internal organs in all of the immersion-exposed channel catfish sampled from 2 hours post-exposure to 48 hours post-exposure, indicating that the invasive capabilities of the attenuated bacteria were intact. However, the infection was limited and all tissues tested were cleared of viable auxotrophic E. ictaluri by 3 days post-exposure. At each sampling time bacterial concentrations in the tissues were significantly higher for wild-type E. ictaluri than for either LSU-E2 or LSU-EI. Maximum tissue levels for the auxotrophic E. ictaluri strain were $10^4$ cfu/gm of tissue at 2 hours post-exposure. All fish tested before the experimental infections were negative for E. ictaluri in any tissues.

The wild-type exposure caused rapid penetration of the host. Head and trunk kidneys had the highest numbers of bacteria per gram of tissue. By 2 hours post-exposure there

TABLE 2

Percent Mortality in Experimental Infections with Wild-type E. ictaluri strain 93-146, Mutant Strain LSU-E1, and Mutant Strain LSU-E2 in Channel Catfish Fingerlings

| Treatment (dose) | 93-146 (Experiment 1) | LSU-E2 (Experiment 1) | 93-146 (Experiment 2) | LSU-E1 (Experiment 2) |
|---|---|---|---|---|
| Immersion ($10^7$ bacteria/ml) | 63.3 | 0.0 | 100 | 0.0 |
| Oral ($10^8$ bacteria/fish) | 20.7 | 0.0 | 26.7 | 0.0 |
| Injection ($10^8$ bacteria/fish) | ND* | 53.3 | ND | 100 |
| Injection ($10^7$ bacteria/fish) | ND | 46.7 | ND | 26.7 |
| Injection ($10^6$ bacteria/fish) | 100 | 0.0 | 100 | 0.0 |
| Injection ($10^5$ bacteria/fish) | 96.7 | 0.0 | 100 | 0.0 |
| Injection ($10^4$ bacteria/fish) | 72.4 | ND | 100 | ND |
| Injection ($10^3$ bacteria/fish) | 56.7 | ND | 73.3 | ND |
| Injection ($10^2$ bacteria/fish) | 55.6 | ND | 43.3 | ND |

*ND = not determined were approximately $10^4$ cfu/gram, and by 6 hours post-exposure approximately $10^6$. Numbers increased to approximately $10^7$ per gram from 3 to 5 days post-exposure. All fish cultured positive at all sampling times. Bacterial concentrations were slightly lower in the spleen than in the kidneys throughout the study, but the difference was not statistically significant. Bacterial counts in the liver did not rise as quickly, and were significantly lower than the other tissues. At 2 hours post-exposure approximately 102 cfu/gram were present in the liver, increasing to approximately $10^4$ at 6 hours post-exposure and remaining at about this level until 2 days post-exposure. Only one of the three fish tested was positive in liver sample at 3 days post-exposure, after which numbers increased dramatically to approximately $10^6$ per gram by 4 days post-exposure.

G. Vaccine Trials on Channel Catfish

*E. ictaluri* aroA. Replicate groups of catfish were vaccinated by immersion in either $10^8$ or $10^9$ cfu/mL of the *E. ictaluri* aroA mutant, LSU-E1. The vaccinated fish were challenged by immersion in $10^8$ cfu/mL of the wild-type strain 93–146 4 weeks after vaccination. Additional replicate groups of fish were booster vaccinated with the mutant after 4 weeks, and were challenged by immersion in $10^8$ cfu/mL of the wild-type strain 4 weeks after the booster. Results are presented in Table 3. Values in the mortality column with the same letter superscript were not significantly different from one another (P<0.01).

TABLE 3

Results of LSU-E1 Vaccine Trials

| Vaccination Dose | Booster Dose (at 4 weeks if given) | Challenge | % Mortality ± St. Dev. |
|---|---|---|---|
| $10^8$ cfu/ml | None | 4 weeks | 39.6 ± 18.5 [b] |
| $10^7$ cfu/ml | None | 4 weeks | 31.2 ± 24.8 [b] |
| $10^8$ cfu/ml | None | 8 weeks | 25.0 ± 13.6 [c] |
| $10^7$ cfu/ml | None | 8 weeks | 50.4 ± 15.0 [b] |
| $10^8$ cfu/ml | $10^8$ cfu/ml | 8 weeks | 17.0 ± 16.4 [c] |
| $10^8$ cfu/ml | $10^7$ cfu/ml | 8 weeks | 22.9 ± 4.2 [c] |
| $10^7$ cfu/ml | $10^8$ cfu/ml | 8 weeks | 4.3 ± 5.0 [d] |
| $10^7$ cfu/ml | $10^7$ cfu/ml | 8 weeks | 4.2 ± 8.3 [d] |
| Non-vaccinated | None | 4 weeks | 86.2 ± 12.8 [a] |
| Non-vaccinated | None | 8 weeks | 75.0 ± 18.0 [a] |

At the 4-week challenge, the vaccinates had significant less mortality than the non-vaccinated fish. At the 8-week challenge, vaccinates without a booster had similar mortality rates as vaccinates at the 4week challenge. However, vaccinates with a booster had significantly less mortality at the 8-week challenge. The best results were obtained with an initial vaccination at $10^7$ cfu/mL, followed by a booster 4 weeks later at either $10^7$ cfu/mL or $10^8$ cfu/mL.

*E. ictaluri* purA. A second study was conducted to evaluate the efficacy of LSU-E2 as a vaccine. One hundred eighty juvenile SPF channel catfish were stocked at a rate of 15 per tank, and were randomly divided into two treatment groups with six tanks per treatment. One treatment group was vaccinated with LSU-E2 *E. ictaluri* by immersion, and the other group was not vaccinated. Two hundred ml of an LSU-E2 overnight culture was added directly to vaccinated tanks, and water flow was stopped for 15 minutes following initial exposure. Bacterial concentration in the water was approximately $3.65 \times 10^7$ cfu/ml.

On day 27 post-vaccination, both vaccinated and non-vaccinated treatments were experimentally infected with wild-type *E. ictaluri* by immersion exposure. *Edwardsiella ictaluri* bacterial culture was added directly to the flow-through tanks for a final bacterial concentration of approximately $5.3 \times 10^7$ cfu/L in the water. Water flow was stopped for 15 minutes following initial exposure and then resumed. Mortalities were recorded each 24 hour period after experimental infection until day 26 post-exposure. Bacterial samples were taken from the trunk kidney of each dead fish, and were cultured on TSA II plates with 5% sheep blood to confirm *E. ictaluri* as the cause of death.

Feeding activity remained normal following immersion vaccination of channel catfish with LSU-E2; no mortalities followed the vaccination. All mortalities following immersion exposure to wild-type *E. ictaluri* were culture positive for *E. ictaluri* from the trunk kidney. Mortality results from the vaccine trial are shown in Table 4. Non-vaccinated tanks had a final average mortality of 33.3%, significantly higher (P<0.01) than the average 11.1% mortality for the vaccinated tanks. The average mortality in the non-vaccinated tanks was significantly higher (P<0.01) than the average for the vaccinated tanks for each day from day 7 post-exposure through the end of the study. Relative percent survival (RPS) of the vaccinated fish compared to the non-vaccinated fish was 66.3 (RPS=100%×(1−[mortality of vaccinated fish/ mortality of control])).

TABLE 4

Results from a single dose LSU-E2 immersion vaccine trial with wild-type *E. ictaluri* immersion challenge

| | Tank | Mortalities | Total fish | Percent mortality | Mean | Standard deviation |
|---|---|---|---|---|---|---|
| Non-vaccinated | 1 | 6 | 15 | 40.0 | | |
| | 2 | 7 | 15 | 46.7 | | |
| | 3 | 8 | 14 | 57.1 | | |
| | 4 | 3 | 15 | 20.0 | | |
| | 5 | 3 | 14 | 21.4 | | |
| | 6 | 2 | 14 | 14.3 | 33.3 | 17.2 |
| Vaccinated | 1 | 1 | 15 | 6.7 | | |
| | 2 | 1 | 15 | 6.7 | | |
| | 3 | 0 | 14 | 0.0 | | |
| | 4 | 4 | 15 | 26.7 | | |
| | 5 | 3 | 15 | 20.0 | | |
| | 6 | 1 | 15 | 6.7 | 11.1 | 10.0 |

The first mortalities occurred in both non-vaccinated and vaccinated tanks on day 6 post-exposure to wild-type *E. ictaluri*. Mortalities steadily increased in the non-vaccinated tanks through day 19 post-exposure. However, no additional mortalities occurred in the vaccinated tanks until day 10 post-exposure, and almost all of the mortalities occurred in the vaccinated tanks between days 10 and 18 post-exposure. The mean time of death for vaccinated fish was 13.9 days, compared to 11.5 days for the non-vaccinated fish.

*E. ictaluri* strain 93–146 has not yet been evaluated for virulence in hosts other than channel catfish. Generally, *E. ictaluri* is somewhat host specific for the North American freshwater catfish family Ictaluridae, with isolates reported from channel catfish (*Ictalurus punctatus*), white catfish (*Ictalurus catus*), and brown bullhead (*Ictaturus nebulosus*). Experimentally exposed golden shiners (*Notemigonus crysoleucas*), largemouth bass (*Micropterus salmoides*), and bighead carp (*Aristichthys nobilis*) were resistant to *E. ictaluri* infection, with tilapia (*Sarotherodon aureus*) being only mildly susceptible to infection. However, *E. ictaluri* has now been reported from several natural outbreaks in non-ictalurid tropical fish, including green-knife fish (*Eigemannia virescens*), danio (*Danio devario*), Rosy barbs (*Puntius conchonius*), and walking catfish (*Clarius batrachus*). In experimental exposure to ESC, European catfish (*Siluris glanis*), rainbow trout (*Oncorhynchus mykiss*), and chinook salmon (*Oncorhynchus tshawytscha*)

were susceptible to infection. No natural epizootics of ESC have occurred in species other than ictalurids. The vaccines reported here are expected to be effective in protecting other species susceptible to infection by E. ictaluri, because the manner in which the vaccine strains were attenuated is not tailored to any specific host.

Production of Attenuated *Pasteurella piscicida* Mutants

We have also successfully cloned and sequenced the *P. piscicida* aroA and purA genes, using the same methods as described above for *E. ictaluri*. A 3464 bp genomic insert carried in plasmid pPD23 has been sequenced; and the aroA gene has been located as bp 439 to 1719 of that insert. The 3463 bp insert has been subcloned into pBluescript to create pPD24, which was digested with the restriction enzyme MseI to remove 144 bp of the aroA gene. Following blunt-end ligation of the 1.7 KB kanamycin marker into the MfeI sites, the insertion/deletion mutant aroA was subcloned into the EcoRI site of the suicide plasmid pGP704, and transferred to a wild-type *P. piscicida* strain by electroporation and homologous recombination.

Analogous techniques will be used to create a ΔpurA: kan mutant of *P. piscicida*.

Mutant ΔaroA: kan (or ΔurA::kan) colonies from double cross-over homologous recombinations were selected on a defined media with aromix (aromatic amino acids and para-amino-benzoic acid) or adenine supplementation, together with selection for kanamycin resistance. Putative mutants were replica plated to minimal media (with kanamycin) without nutrient supplementation to confirm the auxotrophic phenotype. Genetic conformation of the mutant was be confirmed using polymerase chain reaction to amplify fragments with primers internal to the inserted kanamycin marker and primers from the flanking aroA sequence. The primer pairs used amplified the predicated 1208 bp, 1505 bp, and 697 bp. DNA fragments from the aroA mutant, LSU-P2, but not from the wild-type parental strain. DNA sequencing confirmed the interruption of the aroA gene at base pair 236 of the 1281 bp aroA gene, the insertion of the 1710 bp of the Tn903 Kan marker, and the continuation of the aroA gene beginning at base pair 381.

Specific pathogen-free hybrid striped bass obtained from freshwater hatcheries and reared in the specific-pathogen-free culture room of the Aquatic Pathobiology Laboratory of the Louisiana State University School of Veterinary Medicine were used to evaluate the relative virulence of LSU-P2. Fish were stocked into each of sixteen 70liter recirculating systems at 10 ppt salinity and 21–22° C. Challenge procedures for evaluation of virulence of the mutant strain and the wild-type parent strain were conducted as otherwise generally described above for *E. ictaluri*. Mortalities were recorded at 8–12 hour intervals, and all dead fish were necropsied to confirm *P. piscicida* as the cause of death. Using standard bacteriological procedures, LSU-P2 was found to be completely avirulent, in contrast to the high mortality seen with the wild-type parent strain.

Fish of 0.5–0.7 g and 30–50 g will be exposed to one of the mutants or to the wild type by immersion in water containing $10^7$, $10^8$ and $10^9$ bacteria/mL at salinities of 0, 5, 10, and 15 ppt. Each strain/delivery method treatment will be replicated four times with twenty fish per tank, with an additional 4 tanks of non-challenged controls. One fish will be sampled from each tank (i.e., four fish per treatment) at 1, 6, and 12 hours, and then daily for 7 days or until there is no evidence of infection. Samples will be taken from kidney and liver of each fish to determine levels of bacteria in tissue to evaluate the degree of replication and persistence. Concurrent samples will be fixed for histological evaluation of the effect of the mutants on tissues. Data will be analyzed using the general linear models procedure followed by Scheffe's test for individual variables. Bacterial concentration data will be subjected to a logarithmic transformation to stabilize the variances of the sample proportions. If necessary, the salinity limit will be further defined in a second experiment at salinities between the values that are permissive and non-permissive for invasion in the first experiment.

Fish will be reared for thirty days post-vaccination, and then challenged with the virulent parent strain. Separate experiments with 0.2, 5–7, and 50–100 g fish will allow determination of the appropriate dose for each size fish, and the optimal size to administer vaccine. Subsequent experiments will evaluate oral delivery and the use of booster vaccinations.

A sample of the bacterium LSU-P2 was deposited with the American Type Culture Collection (ATCC), 1801 University Boulevard Mansas, Va. 20110–2209 on Apr. 9, 1998, and was assigned ATCC Accession No. 202110. This deposit was made pursuant to a contract between ATCC and the assignee of this patent application, Board of Supervisors of Louisiana State University and Agricultural and Mechanical College. The contract with ATCC provides for permanent and unrestricted availability of the bacterium to the public on the issuance of the U.S. patent describing and identifying the deposit or the publication or the laying open to the public of any U.S. or foreign patent application, whichever comes first, and for availability of the progeny of the bacterium to one determined by the U.S. Commissioner of Patents and Trademarks to be entitled thereto under pertinent statutes and regulations. The assignee of the present application has agreed that if the bacterium on deposit should die or be lost or destroyed when cultivated under suitable conditions, it will be promptly replaced on notification with a viable culture of the same bacterium.

Live-attenuated *E. ictaluri* and *P. piscicida* as Vectors of Heterologous Antigens Because attenuated *E. ictaluri* and *P. piscicida* retain their invasive properties and can be administered by immersion, these attenuated strains are ideal candidates to use as vectors in delivering heterologous antigens for vaccination. The genetic manipulation techniques have been established for attenuated Salmonella strains. The same general techniques will be used here. A number of different genes from bacteria, viruses, parasites, and mammals have been successfully expressed in attenuated Salmonella, and the recombinant strains have been used to immunize small animals. See review in Roberts et al. (1994).

Briefly, the same techniques as described above will be used to create aroA deletion mutants or purA deletion mutants, where the inserted sequences contain both the kanamycin resistance gene to facilitate selection, and also a gene encoding the heterologous antigen. Preferably the gene for the heterologous antigen is placed under the control of the native promoter for the aroA gene or pura gene, as appropriate, to ensure that the antigen is expressed and is 'seen" by the fish immune system during the relatively brief residence of the attenuated strain in the fish before it is cleared. The aroA promoter will be active in conditions where the attenuated *E. ictaluri* is starved for aromatic amino acids; and the purA promoter will be active in conditions where the attenuated *E. ictaluri* is starved for adenine. Alternatively, the gene for the heterologous antigen may be placed under the control of a constitutive promoter, such as the constitutive *E. ictaluri* methylase gene promoter. See Jie Zhang, "Identification, Cloning and Sequence of a Methylase Gene from *Edwardsiella ictaluri*," M. S. Thesis (Louisiana State University, Baton Rouge, 1995). The *E. coli* alkaline phosphatase promoter is also known to be constitutive in *E. ictaluri*.

These vaccines are preferably administered to relatively young fish, most preferably to relatively young fish raised in a specific pathogen free environment, so that the fish will not have already developed immunity to the wild type of the carrier strain (e.g., wild-type *E. ictaluri* or wild-type *P. piscicida*). Such pre-existing immunity could cause the vaccine strain to be cleared from the fish too quickly to establish an immune response to the heterologous antigen.

Examples of heterologous antigens to be used in this aspect of the invention include the several membrane associated proteins from Channel Catfish Virus (CCV). These are encoded by open reading frames 6, 7, 8, 10, 19, 46, 51, and 59 of the CCV genome as described by A. Davison, "Channel Catfish Virus: A new type of herpesvirus," *Virology*, vol. 186, pp. 9–14 (1992); and are all available for subcloning and characterization from a CCV genomic DNA library constructed in the cosmid pHC 79 in our laboratory, L. Hanson et al., "Channel catfish herpesvirus (CCV) encodes a functional thymidine kinase gene: elucidation of a point mutation that confers resistance to Ara-T," *Virology*, vol. 202, pp. 659–664 (1994). Specifically, we have demonstrated that clones pHCCV388, pHCCV389, pHCCV394, and pHCCV395 encompass the entire CCV genome, and that a variety of other clones provide overlapping sequences. Computer analysis of specific locations is underway using the entire CCV sequence (GenBanK Accession No. M75136).

Additional antigens that may be used in this aspect of the invention include, for example, the glycoprotein and ribonucleoprotein gene of infectious hematopoietic necrosis virus (H. Engelking et al., "Glycoprotein from Infectious Hematopoietic Virus (IHNV) induces protective immunity against five IHNV types," *J. Aquatic Animal Health*, vol. 1, pp 291–300 (1989); J. Koener et al., "Nucleotide sequence of a cDNA clone carrying the glycoprotein gene of infectious hematopoietic necrosis virus, a fish rhabdovirus," *J. Virology*, vol. 61, pp. 1342–1349 (1987); and L. Oberg et al., "Bacterially expressed nucleoprotein of infectious hematopoietic necrosis virus augments protective immunity induced by the glycoprotein vaccine in fish." *J. Virology*, vol. 65, pp. 4486–4489 (1991)); and the VP2 major structural and immunogenic proteins of Infectious Pancreatic Necrosis, Genbank Accession Nos. L40580 to L40584 (J. Heppell et al., "Strain variability and localization of important epitopes on the major structural protein (VP2) of infectious pancreatic necrosis virus," *Virology*, vol. 214, pp. 40–49 (1995)).

In each aspect of this invention, it is preferred that the aroA gene or purA gene be disrupted by deletion of a large portion of the gene, as such a mutation minimizes the risk of a spontaneous reversion to virulence. The deletion should preferably encompass at least 10 bases, more preferably at least 100 bases. However, other mutations known in the art that will inactivate or greatly reduce the activity of the gene may also be used. Examples of such mutations include point mutations within the gene or promoter (insertion, deletion, or alteration); insertion of a transposon, mini-transposon, or other sequence into the gene or promoter; or altering the promoter to one that is expressed at much smaller levels. Any such mutation that effectively makes the bacterium an auxotroph will function in the present invention, although it is highly desirable to use a mutation with a minimal risk of reversion to wild type.

As used in the claims, a "protective amount" of an attenuated bacterium is an amount that, when administered to a fish as a vaccine, induces a degree of immunity sufficient to reduce to a statistically significant degree the susceptibility of the fish to infection by a pathogen.

The complete disclosures of all references cited in this specification are hereby incorporated by reference. Also incorporated by reference is the complete disclosure of the following, currently unpublished dissertation: M. L. Lawrence, "Development and In Vivo Evaluation of a PurA Mutant Strain of the Channel Catfish Pathogen *Edwardsiella ictaluri*," Ph.D. Dissertation, Louisiana State University and Agricultural and Mechanical College (May 1997). In the event of an otherwise irreconcilable conflict, however, the present specification shall control.

What is claimed:

1. A vaccine comprising a protective amount of the attenuated *Pasteurella piscicida* bacterium with ATCC accession number 202110.

2. A vaccine comprising a protective amount of an attenuated *Pasteurella piscicida* bacterium, wherein said attenuated *Pasteurella piscicida* bacterium comprises the artificial aroA gene mutation as found in the bacterium with ATCC accession number 202110.

3. The vaccine as recited-in claim 1, wherein said bacterium is the progeny of the bacterium with ATCC accession number 202110; wherein said bacterium has the aromatic amino acid auxotrophic characteristics of the bacterium with ATCC accession number 202110.

4. The vaccine as recited in claim 1, wherein said bacterium additionally comprises an exogenous gene encoding an antigenic peptide or antigenic protein that is native to a fish pathogen other than *Pasteurella piscicida*.

5. A method of reducing the susceptibility of a fish to Pasteurellosis, comprising administering to the fish the vaccine as recited in claim 2.

6. The method as recited in claim 5, wherein the fish is selected from the group consisting of percichthyids, serranids, carangids, balistids, and sparids.

7. The method as recited in claim 5, wherein said administering step comprises immersing the fish in said vaccine.

8. The method as recited in claim 5, wherein said administering step comprises feeding the fish a food product comprising said vaccine.

9. The method as recited in claim 5, wherein said administering step comprises injecting the fish with said vaccine intraperitoneally.

10. The vaccine as recited in claim 2, wherein said attenuated *Pasteurella piscicida* bacterium additionally comprises an exogenous gene encoding an antigenic peptide or antigenic protein that is native to a fish pathogen other than *Pasteurella piscicida*.

11. A method of reducing the susceptibility of a fish to infection by a pathogen that expresses the antigenic peptide or antigenic protein that is encoded by the exogenous gene of the attenuated *Pasteurella piscicida* bacterium comprised in the vaccine of claim 10, comprising administering to the fish a protective amount of said vaccine.

12. The method as recited in claim 11, wherein the fish is selected from the group consisting of percichthyids, serranids, carangids, balistids, and sparids.

13. The method as recited in claim 11, wherein said administering step comprises immersing the fish in said vaccine.

14. The method as recited in claim 11, wherein said administering step comprises feeding the fish a food product comprising said vaccine.

15. The method as recited in claim 11, wherein said administering step comprises injecting the fish with said vaccine intraperitoneally.

* * * * *